United States Patent
Nazarov et al.

(10) Patent No.: US 9,607,819 B1
(45) Date of Patent: Mar. 28, 2017

(54) NON-RADIOACTIVE, CAPACITIVE DISCHARGE PLASMA ION SOURCE AND METHOD

(71) Applicant: The Charles Stark Draper Laboratory Inc., Cambridge, MA (US)

(72) Inventors: Erkinjon G. Nazarov, Lexington, MA (US); Spiros Z. Manolakos, Palm Harbor, FL (US); Francy L. Sinatra, Temple Terrace, FL (US); Timothy A. Postlethwaite, Oldsmar, FL (US); Kenneth A. Markoski, Westford, MA (US); Clayton J. Morris, II, Norfolk, MA (US)

(73) Assignee: The Charles Stark Draper Laboratory Inc., Cambridge, MA (US)

( * ) Notice: Subject to any disclaimer, the term of this patent is extended or adjusted under 35 U.S.C. 154(b) by 0 days.

(21) Appl. No.: 15/014,771

(22) Filed: Feb. 3, 2016

(51) Int. Cl.
  *H01J 49/16* (2006.01)
  *H01J 49/10* (2006.01)
  *H01J 49/04* (2006.01)
  *G01N 27/62* (2006.01)

(52) U.S. Cl.
  CPC .......... *H01J 49/168* (2013.01); *G01N 27/622* (2013.01); *H01J 49/0422* (2013.01); *H01J 49/105* (2013.01)

(58) Field of Classification Search
  CPC ..................................... H01J 49/168
  See application file for complete search history.

(56) References Cited

U.S. PATENT DOCUMENTS

| 5,200,614 | A | * | 4/1993 | Jenkins ............... G01N 27/622 250/282 |
| 5,313,061 | A | | 5/1994 | Drew et al. |
| 5,504,328 | A | | 4/1996 | Bonser |
| 5,767,683 | A | * | 6/1998 | Stearns ............... G01N 27/70 324/449 |
| 6,822,226 | B2 | | 11/2004 | Ross et al. |
| 7,075,067 | B2 | | 7/2006 | Joyce et al. |

(Continued)

OTHER PUBLICATIONS

Laiko, V.V., "Orthogonal Extraction Ion Mobility Spectrometry," *J. Am. Soc. Mass. Spectrom.* 17: 500-507 (2006).

(Continued)

*Primary Examiner* — Michael Logie
(74) *Attorney, Agent, or Firm* — Hamilton, Brook, Smith & Reynolds, P.C.

(57) ABSTRACT

A non-radioactive plasma ion source device includes at least four planar electrodes that define at least three chambers, including a discharger chamber and at least two additional chambers aligned along a major longitudinal axis of the housing. A discharger ionizes at least one of a transport gas and a discharge gas to form ions in the discharger chamber that are directed by a homogeneous electric field generated by the planar electrodes toward an analyte gas outlet. Ionized species of at least one of the transport gas and the discharge gas that are not entrained by a counterflow gas stream are discharged from the discharger chamber to form a stream of ionized particles that ionize a sample gas and thereby form a stream of ionized analyte particles of the same polarity. The ionized analyte particles are entrained with the stream of ionized particles and pass through an analyte gas outlet to an analyzer.

12 Claims, 1 Drawing Sheet

(56) References Cited

U.S. PATENT DOCUMENTS

| | | | |
|---|---|---|---|
| 7,091,481 B2 | 8/2006 | Miller et al. | |
| 7,274,015 B2 | 9/2007 | Miller et al. | |
| 7,279,680 B2 | 10/2007 | Miller et al. | |
| 8,368,011 B2* | 2/2013 | Sakairi | G01N 27/62 250/283 |
| 9,006,678 B2* | 4/2015 | Ivashin | H01J 31/04 250/423 R |
| 9,404,889 B2* | 8/2016 | Munchmeyer | G01N 27/624 |
| 2002/0190201 A1 | 12/2002 | Yamada et al. | |
| 2004/0164238 A1* | 8/2004 | Xu | H01J 49/168 250/287 |
| 2005/0056775 A1* | 3/2005 | Cody | G01N 27/622 250/281 |
| 2005/0196871 A1* | 9/2005 | Cody | G01N 27/622 436/173 |
| 2006/0027746 A1 | 2/2006 | Guevremont et al. | |
| 2007/0075240 A1* | 4/2007 | Hieke | H01J 49/04 250/282 |
| 2008/0210861 A1* | 9/2008 | Wu | G01N 27/624 250/287 |
| 2010/0176290 A1* | 7/2010 | Vidal-De-Miguel | H01J 49/10 250/282 |
| 2011/0018546 A1* | 1/2011 | Kitano | G01N 27/68 324/464 |
| 2011/0095175 A1* | 4/2011 | Bateman | G01N 27/624 250/282 |
| 2012/0160997 A1* | 6/2012 | Fink | H01J 49/10 250/282 |
| 2014/0347062 A1* | 11/2014 | Stearns | G01N 30/64 324/464 |
| 2015/0108347 A1* | 4/2015 | Vidal de Miguel | G01N 27/622 250/288 |

OTHER PUBLICATIONS

Nazarov, E.G., "Pressure Effects in Differential Mobility Spectrometry," *Anal. Chem.*, 78: 7697-7706 (2006).

Ross, S.K., et al. "Reverse Flow Continuous Corona Discharge Ionisation Applied to Ion Mobility Spectrometry," *International Journal of Mass Spectrometry*, 218 L1-L6 (2002).

Sabo, M., et al., "Experimental Simulation of Negative Ion Chemistry in Martian Atmosphere Using Ion Mobility Spectrometry-Mass Spectrometry," *Eur. Phys. J.D.*, 68: 216 (2014).

Seto, Y., et al., "Sensitive Monitoring of Volatile Chemical Warfare Agents in Air by Atmospheric Pressure Chemical Ionization Mass Spectrometry With Counter-Flow Introduction," *Analytical Chemistry*, 85: 2659-2666 (2013).

* cited by examiner

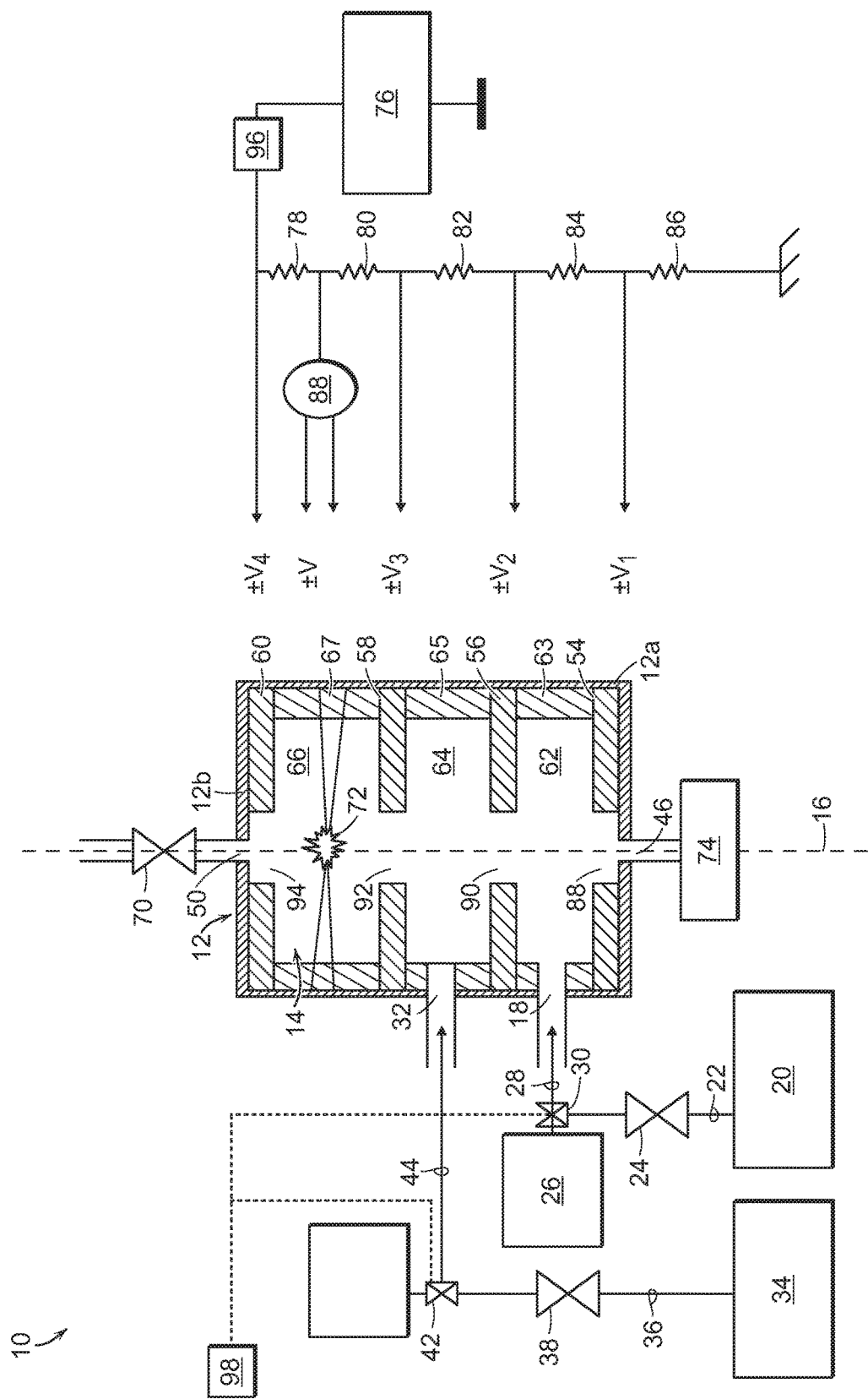

NON-RADIOACTIVE, CAPACITIVE DISCHARGE PLASMA ION SOURCE AND METHOD

BACKGROUND OF THE INVENTION

Ion mobility ionization type instruments (IMS) are employed to detect trace levels of chemicals in gas media. In IMS techniques, vapors of analyte molecules are ionized at ambient conditions, formed into ion species, and then identified by their coefficient of mobility. Conventional IMS ion identification is conducted in moderate direct current (DC) electric fields. In differential ion mobility spectrometry (DMS), which is a derivative of ion mobility technology, ion separation occurs by control of trajectories when ions move under the superimposed effect of a gas stream and a strong asymmetric waveform alternating current (AC) electric field. IMS and DMS are able to operate at atmospheric pressure conditions and, therefore, do not require cumbersome and high-power-consuming gas evacuating (pumping) equipment, thereby lending some portability to these instruments. Handheld prototypes of highly sensitive gas analyzers have been built, and numerous iterations are currently available. Historically, ion mobility-based instruments have been adapted for military, homeland security and space investigation applications. Currently, ion mobility technology is more and more involved in many civilian applications, such as chemical and biological processes control applications, for medical diagnostic applications, and for environmental control applications.

Typically, radioactive ion sources are employed by ion mobility sensors to ionize chemicals in a vapor state. Such sources often employ steel foil that has been implanted with radioactive isotopes, such as americium ($^{240}$Am), nickel ($^{63}$Ni), or tritium ($^{3}$H). These ion sources are very convenient for field applications because they don't require large amounts of power, are lightweight, and are stable in operation. They also can provide both polarity ion species of either positive or negative charged ion species from analyzed ions. Nevertheless, the storage, transportation, periodic certification, disposal and safety requirements for using radioactive sources are generally highly regulated, which significantly increases the cost of operation and narrows potential applications, especially in various civilian applications.

Currently available non-radioactive methods of ion generation include corona discharge, ultraviolet (UV) ionization, and radiofrequency (RF) discharge ionization, including electromagnetic induction and capacitive gas discharge (CGD) methods. Known methods of these techniques all include limitations. For example, corona discharge often is not stable in the long term and can contaminate the sample with metal ions or nitrogen oxides ($NO_x$), thereby interfering with analytical results. UV ionization typically is a more straightforward method of generating ions, but typically is limited to low or only moderate ionization energies, thereby limiting the types of molecules that can be ionized. RF discharge ionization methods, which include AC circuits, such as inductive and capacitive discharge techniques, also have their limitations. For example, electromagnetic induction methods typically are limited to high-powered discharges, such as are employed during production of refractory materials, abrasive powders, and the like. Most available CGD methods generally do not allow for ion source parameter optimization, such as minimization of plasma temperature to eliminate formation of nitric oxide ($NO_x$) and ozone ($O_3$) species due to plasma chemistry. These species have high electron affinity and therefore can capture free electrons from plasma, thereby resulting in the presence in the reaction chamber of these undesirable ion species, and reduced (or even fully suppressed) sensitivity to detection of negative ion species derived from analyte molecules.

Therefore, a need exists for a method of ion generation that overcomes or minimizes the above-referenced problems.

SUMMARY OF INVENTION

The invention generally is directed to a non-radioactive plasma ion source and a method for generating analyte ions of either positive or negative charge from a non-radioactive ion source.

In one embodiment, the invention is a non-radioactive plasma ion source that includes a housing, at least four planar electrodes mounted along a major longitudinal axis of the housing, and a non-radioactive discharger. The housing includes an interior volume having a major longitudinal axis, a first gas outlet for introduction of a transport gas, a second gas outlet for introduction of a discharge gas, a counterflow gas outlet and an analyte gas outlet. The planar electrodes mounted along the major longitudinal axis of the housing are located between the counterflow gas outlet and the analyte gas outlet, thereby partitioning the interior volume into at least three chambers, including a discharger chamber, a first gas inlet chamber, and a second gas inlet chamber. The chambers are aligned along the major longitudinal axis between the counterflow gas outlet and the analyte gas outlet. Each of the planar electrodes defines an opening for mounting a homogeneous electric field by application of a DC voltage to the electrodes, wherein fluid communication is provided between the counterflow gas outlet and the analyte gas outlet through the openings in the chambers, and wherein the first gas inlet and the analyte gas outlet are at the first gas inlet chamber, the counterflow gas outlet is at the discharger chamber, and the second gas inlet and second gas inlet chamber are between the discharger chamber and the first gas inlet chamber. The non-radioactive discharger is located within the discharger chamber for generating an ionized non-radioactive plasma, whereby an ion species is selected by exposure of the ionized plasma to a homogeneous electric field and by exposure to at least one of a transport gas stream and a delivery gas stream that form a counterflow gas stream which is discharged through the discharge gas outlet. The selected ion species is directed by the homogeneous electric field into combination with a sample gas that is directed into at least one of the first gas inlet and the second gas inlet, thereby forming an analyte ion species from the sample gas. The analyte then is discharged with the selected ion species through the analyte gas outlet.

In another embodiment, the invention is a method of generating analyte ions of either positive or negative charge with a non-radioactive source. The method includes generating an ionized plasma at a non-radioactive discharger within a discharger chamber defined in-part by a housing, wherein the ionized plasma includes positive ions, negative ions and electrons. A homogeneous electric field is generated by application of distributed direct current voltages to at least four planar electrodes, wherein the at least four planar electrodes are mounted along a major longitudinal axis of a housing that defines an interior volume, a first gas inlet for introducing a transport gas, a second gas inlet for introducing a discharge gas, a counterflow gas outlet, and an analyte gas outlet, wherein the four planar electrodes partition the interior volume into at least three chambers, including a discharger chamber, a first gas inlet chamber and a second gas inlet chamber, the chambers being aligned along the major longitudinal axis between the counterflow gas outlet and the analyte gas outlet. Each of the electrodes define an opening, whereby fluid communication is provided between the counterflow gas outlet and analyte gas outlet through the openings in the chambers. The first gas inlet and the analyte gas outlet are at the first gas inlet chamber, the first gas outlet is at the discharger chamber, and the second gas inlet and the second gas inlet chamber are between the discharger chamber and the first gas inlet chamber. The electric field causes at least a portion of the charged particles of the ionized plasma to move from the discharger chamber through the second and first gas inlet chambers to the analyte gas outlet. At least one of a transport gas and a discharge gas is directed, through the first gas inlet into the first-gas inlet chamber or through the second gas inlet into the second gas inlet chamber, respectively, whereby at least a portion of the transport gas or the discharge gas, or the combination of the transport gas and the discharge gas, is directed through the discharger chamber and the counterflow gas outlet, whereby at least one of the transport gas and the discharge gas separates the charged from the oppositely charged particles formed in the discharger chamber, and directs the oppositely charged particles through the counterflow gas outlet. A sample gas is directed through at least one of the first gas inlet and the second gas inlet, into at least one of the respective first and second gas inlet chambers, whereby the charged particles ionize the sample gas to form an analyte gas of resulting ionized analyte gas particles. Analyte gas particles having the same electrical charge as that of charged particles are directed through the analyte gas outlet, along with the charged particles.

In still another embodiment, the invention is a method of generating ion species in a gas medium from a non-radioactive ion source. In this environment, a plasma is generated with any type of non-radioactive ion source (such as a corona, capacitive discharge plasma source (CDPS), sparks, carbon nanotubes or an emitter) within a discharger chamber defined in-part by a housing, the ionized plasma including, for example, a variety of positive and negative charged ions, neutral molecules, chemical complexes, and electrons. A homogeneous direct-current electric field is generated by applying a plurality of DC voltages to a sequence of distributed planar electrodes, isolated from each other by dielectric spacers, each defining a central opening along a major longitudinal axis of a housing that defines at least three chambers along the major longitudinal axis, including a discharger chamber, a first gas inlet chamber, and a second gas inlet chamber, wherein each of the electrodes are separated by a dielectric wall whereby gas fluid communication is provided by creation of a counterflow gas stream in a second gas inlet chamber which, through an opening in one of the electrodes, is directed to the discharger chamber for cleaning of the plasma and by creation of a transport gas flow stream in the first gas inlet chamber which, through an opening in another of the electrodes, is directed, along with analyte ions formed by exposure to the homogeneous direct current electric field and by ions of the non-radioactive ion source, towards an analyte outlet. The homogeneous direct current electric field and the counterflow gas stream are adjusted to extract from the plasma only a targeted reactant species component of the plasma to thereby cause at least a portion of ionized plasma to move from the discharger chamber through the second and first gas inlet chambers. A sample gas is directed through at least one of the first gas inlet and the second gas inlet, whereby molecules of the sample gas are ionized by exposure to the charged reactant species generated and extracted from the plasma, to thereby form analyte gaseous ions that are directed through the analyte gas outlet to an analyte gas analyzer.

This invention has many advantages. For example, embodiments of the present invention include a device and method of generating a non-radioactive capacitive discharge plasma ion source for effective ionization of gas samples. Features that factor into one operational regime of the invention include substantial gas counterflows for cleaning of plasma from molecular and ion particles of both polarities (which form due to plasma chemistry), and which draw and direct only electrons into a reaction chamber, to form an electron beam that is used to formation negative ions. In a positive mode, a gas counter flow is employed to clean plasma from only heavy ions and neutral molecules. By adjusting the rate of flow of counter flow gas, conditions can be obtained where, for example, only Reactant Ion Peak (RIP) species that have relatively small collision-cross-sections (CCS) are directed in to the reaction chamber. Examples of such RIP species include $(H_2O)_n H^+$ where n=1, 2, 3. In the controlled conditions of the reaction chamber of the invention, independently introduced vapor analyte molecules are directed through an inlet into the reaction chamber and interact with electrons or positive RIP ions to form analyte ions, which can then be analyzed with spectral analytical measurements (such as DMS, IMS, MS, etc.). The ionization source of the invention can be developed for use with portable gas analyzers to replace radioactive ion sources typically used in such systems. The device and method of the invention provides gas phase chemistry to form positive and negative ion species identical to those formed in radioactive ion sources, where ionization of gas molecules occur due to continuously radiated alpha, beta or gamma particles from radioactive isotopes.

The method and device of the invention are capable of efficiently forming positive and negative ion species, that avoid legal and technological restrictions for ion source use and transportation to which radioactive sources typically are subject. Further, the risk of orphaned (i.e., stolen or lost) sources and accidental exposure is reduced. Also, the device and method for generating a plasma source of the invention typically has lower operating costs and administrative expenses than radioactive counterparts. In addition, the method and device of the invention has many civilian applications within the field of IMS technology in sensitive industries and applications, such as: air quality monitoring in commercial and residential applications, including industries such as power, oil and gas refining, and pharmaceutical and wastewater applications; food production and monitoring; personalized medicine applications; noninvasive breath analyses, or noninvasive medical and physiological diagnoses; forensic applications, including search and rescue operations; and biometrics.

Either or both of the discharger and the transport gases can be, for example, similar or different gases. For example, it may be dry and purified air, or nitrogen, with or without gas modifiers, which significantly reduces expense and improves portability. Further, by employing at least four planar electrodes defining at least three chambers, including a first gas inlet chamber and a second gas inlet chamber, aligned along a major longitudinal axis of a housing, and by controlling flow of an analyte gas into either or both of the first gas inlet chamber and second gas inlet chamber, and of flow of either or both of the transport and discharge gases, whether they be of the same or different compositions, control over ionization of the analyte gas is enhanced, and refinement of ionized species generated in the discharger chamber as they are conducted toward the analyte outlet is significantly improved.

The apparatus and method of the invention can be operated in either a negative mode, where the planar electrodes within the chamber have negative electrical potentials, or a positive mode, where the planar electrodes within the chamber are under a positive electrical potential. In the negative mode, counterflow within the chamber improves gas-phase chemistry, while the positive mode helps to eliminate chemical noise from heavy components which can be in the source sample gas.

BRIEF DESCRIPTION OF THE DRAWINGS

The FIGURE is a schematic representation of one embodiment of the non-radioactive plasma ion source device of the invention.

DETAILED DESCRIPTION OF THE INVENTION

The foregoing will be apparent from the following more particular description of example embodiments of the invention, as illustrated in the accompanying drawing. The drawing is not necessarily to scale, emphasis instead being placed upon illustrating an embodiment of the present invention.

The invention generally is directed to a non-radioactive plasma ion source device and method of generating ions with a non-radioactive source. In one embodiment, the method is conducted under ambient conditions. Planar electrodes of the device, in combination with a discharger chamber, and first and second gas inlet chambers are aligned along a major longitudinal axis of a housing between a counterflow gas outlet and an analyte gas outlet. A method of operation of the non-radioactive plasma ion source device of the invention enables ionization of an analyte gas directed into either or both of the first and second gas inlet chambers with ions generated in the discharger chamber and conducted along an electric field generated by the four planar electrodes. Enhanced control over interaction between the plasma ions and gases directed into the first and second chambers, respectively, in combination with control over an electric field generated by the planar electrodes, increases the efficiency of ionization of the analyte gas and the purity of an analyte gas flow being discharged through an analyte gas outlet opposite a counterflow gas outlet.

In one embodiment, non-radioactive plasma ion source device 10 includes housing 12 having first end 12a end second end 12b. Housing 12 defines interior volume 14 and has major longitudinal axis 16. Housing 12 and tubular spacer 63 define first gas inlet 18 for introduction of transport gas from transport gas source 20 through conduit 22 that is regulated by valve 24. Housing 12 is constructed of a suitable dielectric material, such as is known in the art.

Sample source 26 is in communication with the first gas inlet 18 through line 28. Valve 30 controls the relative flow of transport gas from transport gas source 20 and from sample source 26 through first gas inlet 18. Housing 12 and tubular spacer 65 define second gas inlet 32. Flow of discharge gas from discharge gas source 34 through line 36 and valve 38, and flow of sample gas from sample source 40 are controlled by valve 42. Sample gas from sample gas source 40 and discharge gas from discharge gas supply 34 are selectively metered through line 44 and second gas inlet 32. Housing 12 also defines analyte gas outlet 46 at first end 12a of housing 12, and counterflow gas outlet 50 at second end 12b of housing 12.

Planar electrodes 54, 56, 58, and 60 are distributed along a length of housing 12 from first end 12a to second end 12b of housing 12. Each of planar electrodes 54, 56, 58, and 60 define openings 88, 90, 92, and 94, respectively, and are electrically isolated from each other within housing 12 by tubular dielectric spacers 63, 65, and 67, respectively. Spacers 63, 65, and 67 are constructed of a suitable material, such as is known in the art. Examples of suitable materials of spacers 63, 65, and 67, include polyether ether ketone (PEEK), which exhibits relatively little off-gassing. Optionally, spacers 63, 65, and 67 can be constructed of a suitable semiconducting material, such as is known to those skilled in the art. Openings 90 and 92 provide fluid communication between the chambers 62, 64, and 66, defined by housing 12, by tubular dielectric spacers 63, 65, and 67, and by planar electrodes 54, 56, 58, and 60. In one embodiment, electrodes 54, 56, 58, and 60 are circular and define circular openings 88, 90, 92, and 94, respectively.

Planar electrodes 54, 56, 58, and 60 are fabricated of a suitable conductive material of construction, such as stainless steel. Planar electrodes 54 and 56, in combination with spacer 63, define first gas inlet chamber 62. First gas inlet 18 and analyte gas outlet 46 are in fluid communication with first inlet chamber 62. Planar electrodes 56 and 58, together with housing 12 and spacer 65, define second gas inlet chamber 64. Second gas inlet 32 is in fluid communication with second gas inlet chamber 64. Planar electrodes 58 and 60, together with spacer 67, define discharger chamber 66.

Counterflow gas outlet 50 is in fluid communication with discharger chamber 66. Valve 70 at counterflow gas flow outlet 50 regulates flow of counterflow gas through counterflow gas flow outlet 50. Discharger 72 is located within discharger chamber 66. Discharger 72 is at least one member of the group consisting of a carbon nanotube ionization source, a capacitive gas discharge plasma ionization source, a corona ionization source, and a dielectric-barrier discharge ion source.

In one embodiment of the invention, gas delivery within the chambers is a uniform circumferential gas delivery that provides uniform gas flow in the homogenous direct current electric field, and uniform gas flow through the chambers.

Analyzer 74 is in fluid communication with analyte gas outlet 46. An example of a suitable analyzer is, for example, a spectral detector. Examples of suitable spectral detectors include at least one member of the group consisting of an ambient-pressure ion mobility spectrometer, such as a differential ion mobility spectrometer a time-of-flight ion mobility spectrometer, aspiration ion mobility spectrometer and ambient-pressure ionization mass spectrometer.

Planar electrodes 54, 56, 58, 60 are in selective electrical communication with direct current (DC) power supply 76 through electric resistors 78, 80, 82, 84, and 86. Electrical resistors 78, 80, 82, 84, and 86 electrically partition planar electrodes 60, 58, 56, and 54, respectively, whereby the voltage applied to planar electrodes 60, 58, 56, and 54 is incrementally reduced at each successive resistor 78, 80, 82, 84, and 86. Resistor 86 is employed to adjust the electrical potential between discharger 72 and analyzer 74. Adjusting this electrical potential assists in optimizing conditions for ion transmission from discharger 72 to analyzer 74, and the value of this voltage ($V_1$) depends on the type of analyzer that is employed. Discharger 72 is in selective electrical communication with AC voltage generator 88, which is needed for generation of plasma in discharger chamber 66.

DC power supply 76 can provide either a negative voltage or a positive voltage to planar electrodes 54, 56, 58, and 60. Rf voltage generator 88 provides AC voltage pulses to generate plasma between two electrically isolated wires (e.g. cross-wire (CW) discharger), by switching polarity of DC power supply 76, whereby positive or negative ion species can be directed from discharger chamber 66 to ionization chamber 62.

An important parameter to consider is the electric field (E), and the homogeneity of the electric field that is formed in each chamber as a result of the voltages applied to the electrodes. Electric field E=V/L in a planar design, can be, for example, 100 V/cm. The following Tables 1 and 2 are representative listings of suitable applied voltages and corresponding distances between planar electrodes in one embodiment of the invention when methyl salicylate (MS) is the analyte.

TABLE 1

Electric field distribution

| | Voltage (V) | Distance between Voltages (mm) | Electric Field (V/mm) ($V_{differential}$/Distance) |
|---|---|---|---|
| V4 (electrode 60) | −700 | | |
| Plasma Offset (72-discharger) | −525 | 6.50 | 26.9 |
| V3 (electrode 58) | −425 | 6.50 | 15.4 |
| V2 (electrode 56) | −300 | 8.80 | 14.2 |
| V1 (electrode 54) | −150 | 8.80 | 17.0 |
| Sensor (ground) | 0 | 4.40 | 34.1 |

TABLE 2

| Suitable Voltages for total ion current in negative mode | | Suitable Voltages for total ion current in positive mode | | Suitable Analyte (Methyl Salicylate) Response for one set of voltages working in both polarities | |
|---|---|---|---|---|---|
| Electrode | Voltage (V) | Electrode | Voltage (V) | Electrode | Voltage (V) |
| V4 (electrode 60) | −700 | V4 (electrode 60) | +700 | V4 (electrode 60) | +/−700 |
| Plasma Offset (72-discharger) | −525 | Plasma Offset (72-discharger) | +525 | Plasma Offset (72-discharger) | +/−525 |
| V3 (electrode 58) | −490 | V3 (electrode 58) | +390 | V3 (electrode 58) | +/−415 |
| V2 (electrode 56) | −300 | V2 (electrode 56) | +280 | V2 (electrode 56) | +/−300 |
| V1 (electrode 54) | −150 | V1 (electrode 54) | +160 | V1 (electrode 54) | +/−150 |
| Sensor (ground) | 0 (ground) | Sensor (ground) | 0 | Sensor (ground) | 0 |

Controller 96 controls the polarity and total value of DC voltage of direct current to planar electrodes 54, 56, 58, and 60. The values of resistors 78, 80, 82, 84, and 86 are regulated to optimize transmission of ions or electrons from discharger chamber 66 to first gas inlet chamber 62. Typically, resistor 78 is a two mega ohm resistor, and the values of resistors 80, 82, 84, and 86 are regulated accordingly.

Controller 98 controls at least one member of the group consisting of: a rate of flow of sample gas from sample source 26 and sample source 40 into at least one of first gas inlet 18 and second gas inlet 32, respectively; a rate of flow of transport gas from transport gas source 20 into first gas inlet 18; and a rate of flow discharge gas from discharge gas source 34 into second gas inlet 32, by controlling a suitable one or more of valves 24, 30, 38 and 42. By controlling the rates of flow of sample gas into either or both of first gas inlet 18 and second gas inlet 32, and relative rates of flow of transport gas and discharge gas into first gas inlet 18 and second gas inlet 32, respectively, the gas flow rate at discharge chamber 66 is controlled. Additional control is provided by regulating counterflow regulator 70, either independently or in conjunction with controller 98.

In a method of the invention of generating ions with a non-radioactive source, ionized plasma is generated at non-radioactive discharger 72 within discharger chamber 66. The ionized plasma is formed by ionization of gas present within housing 12 and, specifically within discharger chamber 66. Ionization in discharge chamber 66 can occur, optionally, under ambient temperature and pressure conditions, standard temperature and pressure conditions, or at temperature and pressures conditions that are each independently, ambient, standard, or other then either ambient or standard. The source of gas present within housing 12 is at least one of discharge gas supplied from discharge gas supply 34 and transport gas supplied from transport gas supply 20. Alternatively, gas present within housing 12 is filtered ambient gas supplied from the atmosphere surrounding housing 12 that is admitted into housing 12 through at least one of the first gas inlet 18 and second gas inlet 32. An example of a suitable gas provided by discharge gas supply 34 and transport gas supply 20 includes air that has been purified of contaminants other than, for example, nitrogen, oxygen and carbon dioxide. The gases of transport gas supply 20 and of discharge gas supply 34 can be the same gas or different gases, and can be pressurized. In some embodiments, the discharge gas source 34 and the transport gas source 20 each independently can include a dopant (gas modifier), such as hydrogen, water molecules, at least one nobel gas, and traces of polar, small chemical molecules (e.g. acetone, isopropanol, and acetonitrile, and so forth).

In one embodiment, ambient air is directed into housing 12 through at least one of first gas inlet 18 and second gas inlet 32, following purification by directing the ambient air through a suitable filter, such as a suitable molecular sieve filter known in the art.

In another embodiment, each gas is delivered to its chambers via a circumferential distribution manifold which exits into the chambers via a thin uniform gap.

Controller 96 controls the polarity of planar electrodes 54, 56, 58, and 60, whereby all of the planar electrodes have either a positive charge or a negative charge. The strength of the electrical charge of each of planar electrodes 54, 56, 58, and 60 relative to each other is determined by the resistance of resisters 84, 82, 80, and 78, respectively. Discharger 72 is operated by actuation of electrical connection between discharger 72 and DC power supply 76 through AC converter 88. The frequency of alternation of alternating current converter 88 typically is in a range of between about 11 mhz. Typically, the rate of ion pulsation is between about 0.3-1.5 khz.

The non-radioactive plasma ion source of the invention can be operated in either of two modes. In a first mode, all planar electrodes 54, 56, 58, and 60 are negatively charged. In a specific embodiment, ambient air, either purified or not purified, is directed into housing 12, either directly from the atmosphere surrounding the device, or from at least one of transport gas supply 20 and discharge gas supply 34. Ambient air at discharger 72 within discharging chamber 66 is ionized by discharger 72 to generate the following negatively charged reactant ions: $NO_2^-$, $NO_3^-$, $(H_2O)NO_3^-$, and $(NO_2)NO_2^-$. Ionization is conducted under suitable conditions, such as are known in the art, such as at ambient temperature and pressure, or at normal temperature and pressure conditions. Other ionized species formed include $O_2^-$ and electrons. Electrification of planar electrodes 54, 56, 58, and 60 creates a homogeneous electric field that, because of the incrementally decreased electrical charge of each of the planar electrodes with application of each resistor 78, 80, 82, 84, and 86, negatively charged ions generated by discharger 72 migrate from discharger 72 toward analyte gas outlet 46, thereby forming a stream of negatively charged particles flowing in the homogeneous electric field from discharger 72 toward analyte gas outlet 46.

Ambient air is flowed into either or both of first gas inlet 18 and second gas inlet 32 or, alternatively, transport gas is flowed from transport gas source 20 through line 22 and line 28 into housing through first gas inlet 18 and, either in addition or as an alternative, flow of discharge gas is directed from discharge gas source 34 through lines 36 and 44 into housing 12 through second gas inlet 32. Any or all of these gas flows create a flow of a counterflow gas stream toward second end 12*b* of housing 12, and out of housing 12 through counterflow gas outlet 50. The rate of flow of the counterflow gas stream through counterflow gas outlet 50 is regulated by counterflow regulator valve 70. The rate of flow of transport gas from transport gas source 20 and of discharge gas from discharge gas source 34 is regulated through valves 24 and 38, respectively and, alternatively, or in addition, by operation of valves 30 and 42, respectively, by controller 98.

The counterflow gas stream formed within housing 12 from analyte gas source 26 or analyte gas source 40, or a combination of both, and at least one of transport gas from transport gas source 20 and discharge gas source 34 which, in addition to providing a source for ionization of gas by discharger 72, also causes undesired ionized species formed at discharger 72, such as nitrogen-based ionized species, generally having the formula of $NO_x$, wherein x can be an integer x=1, 2, 3, to be entrained with the non-ionized portion of the counterflow gas stream and thereby be directed with the counterflow gas stream through counterflow gas outlet 50 and counterflow regulator valve 70. Remaining ionized species, namely $O_2^-$ and electrons, which have a smaller profile than $NO_x$ species, remain within the stream of negatively charged species directed by a relatively homogeneous electric field generated by planar electrodes 54, 56, 58 and 60, from discharger 72 where they are formed, to analyte gas outlet 46, substantially without interference by the counterflow gas stream directed in the opposite direction toward counterflow gas outlet 50.

Sample gas is directed into housing 12 from at least one of sample source 26 and sample source 40 through lines 28 and 44, respectively, and then through first gas inlet 18 and second gas inlet 32, respectively, into housing 12. In various embodiments, sample gas from sample source 26 can be metered through first gas inlet 18 by combination with transport gas from transport gas supply 20 by regulation of valve 30, which is controlled by controller 98. In other embodiments, sample gas from sample source 40 can be metered into housing 12 by combination with discharge gas from discharge gas source 34 at valve 42, which is controlled by controller 98. In other embodiments, sample gas from sample gas sources 26 and 40 is directed into housing 12 through both first gas inlet 18 and second gas inlet 32. Examples of suitable gases at sample sources 26 and 40 include, for example, at least one of benzene, toluene ethyl benzene (BTEX), methyl salicylate, and xylene, a stimulant of chemical warfare agents (CWA), and explosives. Once sample gas has been directed into housing 12 from whatever source, either from sample source 26 or sample source 40, or both, the sample gas within housing 12 is ionized to form a stream of ionized analyte particles by interaction or reaction of the sample gas with the stream of ionized particles directed by planar electrodes 54, 56, 58, and 60 from discharger 72 toward analyte gas outlet 46. While not wishing to be bound by any particular theory, it is believed that control of the rate of flow of sample gas through at least one of the first gas inlet 18 and second gas outlet 32, in combination with selective introduction of transport gas through first gas inlet 18 and introduction of discharge gas through second gas inlet 32, within a homogeneous electric field generated by the planar electrodes 54, 56, 58, and 60 defining at least three chambers, namely first inlet gas chamber 62, second gas inlet chamber 64 and discharger chamber 66, results in a highly purified stream of ionized particles consisting essentially of desired particles having a relatively small cross-section, and having reduced electron affinity. This steam of ionization particles then ionizes the sample gas and, because of its purity, substantially attenuates suppression of the efficiency of analyte ion formation during interaction with the sample gas. The resulting stream of ionized analyte particles is of generally greater purity and formed with greater efficiency than streams of ionized analyte particles formed by methods known in the art. The ionized analyte stream formed by interaction of sample gas with the ionized stream formed is then directed through analyte gas outlet 46 for analysis by analyzer 74.

In a second, or positive, mode, planar electrodes 54, 56, 58, and 60 are under positive potentials. At least one of the transport gas source 20 and the discharge gas source 34 can be, for example, purified air, a noble gas, nitrogen gas, or some other suitable gas. For example, if air is employed, reactant ions generated by discharger 72 that are formed and subsequently directed from discharger 72 through analyte gas outlet 46 include $(H_2O)_2H^+$ $(H_2O)_3H^+$, $(H_2O)_4H^+$, or, generally, reactive ion species having the general formula of $W_nH^+$ (where "W" means a water molecule). The reactant ion species, $W_nH^+$, are generally referred to as protonated water clusters. As in the first, or negative, mode, ionization can be conducted at ambient or normal conditions, such as at ambient or normal temperature and pressure conditions. A desirable positively charged species for interaction and reaction with a sample to form positively charged analyte ion species include $MH^+$, $M_2H+$, $MWH+$, where "M" is an analyte molecule. In this embodiment, at least one of the transport gas and discharge gas, or ambient air, whether filtered or unfiltered, is directed into housing 12 through at least one of first gas inlet 18 and second gas inlet 32 and forms a counterflow gas stream that provides a source of gas to be ionized by discharger 72. The undesirable positively charged ion species are carried with the counterflow gas stream through counterflow gas outlet 50 and counterflow regulator valve 70.

Remaining, desirable positively charged ion species, that are not entrained by the counterflow gas stream, are directed by the homogeneous electric field generated by planar electrodes 54, 56, 58 and 60 toward analyte gas outlet 46 and, in doing so, interact with sample gas directed into housing 12 through at least one of first gas inlet 18 and second gas inlet 32 to thereby ionize the sample gas and form ionized analyte particles. Positively charged analyte particles are directed with the positively charged particles with which they interact toward and through analyte gas outlet 46 for analysis by analyzer 74. As with operation of the invention by generation of a negatively charged homogeneous electric field, it is believed, without being limited to any particular theory, that selective control of transport gas and discharge gas into housing 12 through first gas inlet 18 and second gas inlet 32, respectively, along with selective introduction of a sample gas through at least one of first gas inlet 18 and second gas inlet 32 provides, in combination with a relatively homogeneous electric field generated by at least four planar electrodes, defining at least three chambers, a substantially pure stream of desirable positively charged particles that ionize the sample gas with greater efficiency to thereby form a stream of positively charged analyte particles for analysis at analyzer 74. The purified stream of ionized analyte particles, whether negatively charged or positively charged, is thereby generated with greater efficiency, and with fewer impurities, than is possible by use of other non-radioactive sources.

In either the positive or negative mode, one embodiment of the method of the invention includes introduction of gas sample (i.e., source of analyte gas) only from sample gas source 26 through inlet 18, while discharge gas is directed from discharge gas source through inlet 32. Transport gas, in this embodiment, is optionally employed. The discharge gas and the transport gas may be different gases or the same gas. In another embodiment, sample gas is directed into inlet 32, while at least one of the discharge gas and transport gas are directed into inlets 32 and 18, respectively. In still another embodiment, sample gas is directed into both inlets 18 and 32, while at least one of transport gas and discharge gas are directed through inlets 18 and 32, respectively.

The relevant teachings of all patents, published applications and references cited herein are incorporated by reference in their entirety.

While this invention has been particularly shown and described with reference to example embodiments thereof, it will be understood by those skilled in the art that various changes in form and details may be made therein without departing from the scope of the invention encompassed by the appended claims.

What is claimed is:

1. A non-radioactive plasma ion source, comprising:
   a) a housing, defining
      i) an interior volume having a major longitudinal axis,
      ii) a first gas inlet,
      iii) a second gas inlet,
      iv) a counterflow gas outlet, and
      v) an analyte gas outlet;
   b) at least four planar electrodes mounted along the major longitudinal axis of the housing between the counterflow gas outlet and the analyte gas outlet, thereby partitioning the interior volume into at least three chambers, including
      i) a discharger chamber,
      ii) a first gas inlet chamber, and
      iii) a second gas inlet chamber,
      the chambers being aligned along the major longitudinal axis between the counterflow gas outlet and the analyte gas outlet, each of the planar electrodes defining an opening for creating a homogeneous electric field by application of a direct current voltage to the electrodes, wherein fluid communication is provided between the counterflow gas outlet and the analyte gas outlet through the openings and the chambers, and wherein the first gas inlet and the analyte gas outlet are at the first gas inlet chamber, the counterflow gas outlet is at the discharger chamber, and the second gas inlet and the second gas inlet chamber are between the discharger chamber and the first gas inlet chamber; and
   c) a non-radioactive discharger between two of the planar electrodes, that generates an ionized plasma within the discharger chamber for exposure to the homogenous electric field, whereby a selected ion species is directed by the homogenous electric field into combination with a sample gas that is directed into at least one of the first gas inlet and the second gas inlet, the combination thereby forming analyte ion species of an analyte gas that is discharged through the analyte gas outlet.

2. The ion source of claim 1, wherein the discharger includes at least one member of the group consisting of a carbon nanotube ionization source, a capacitive gas discharge plasma ionization source, a corona ionization source, and a dielectric-barrier discharge ion source.

3. The ion source of claim 1, further including:
   a) a direct current power source in selective electrical communication with the planar electrodes, whereby the planar electrodes generate an electric field within the housing; and
   b) an alternating current power source in electrical communication with the discharger.

4. The ion source of claim 3, further including electrical resistors between the planar electrodes, whereby voltages applied by direct current to the electrodes decreases from the discharger chamber to the first gas inlet chamber.

5. The plasma ion source of claim 4, further including a controller that controls the direct current to the planar electrodes.

6. The plasma ion source of claim 1, further including a spectral detector at the analyte gas outlet, the spectral detector measuring ions discharged through the analyte gas outlet.

7. The ion source of claim 6, wherein the spectral detector includes at least one member of the group consisting of an ambient-pressure ion mobility spectrometer, a differential mobility spectrum analyzer, a time-of-flight ion mobility spectrometer, and an ambient-pressure ionization mass spectrometer.

8. The ion source of claim 1, further including a controller that controls at least one member of the group consisting of a rate of flow of sample gas into at least one of the first gas inlet and the second gas inlet, a rate of flow of transport gas into the first gas inlet, and a rate of flow a discharge gas into the second gas inlet.

9. The ion source of claim 8, wherein the controller is an electrical circuit that includes at least one member of the group consisting of a pulse generator, a resonance generator and a resonant circuit.

10. The plasma ion source of claim 1, further including at least one transport gas source in selective fluid communication with the first gas inlet.

11. The plasma ion source of claim 1, further including at least one discharger gas source in selective fluid communication with the second gas inlet.

12. The ion source of claim 1, further including a counterflow regulator at the counterflow gas outlet.

* * * * *